United States Patent
Dickerhoff et al.

(10) Patent No.: US 12,090,071 B2
(45) Date of Patent: Sep. 17, 2024

(54) VASCULAR PROSTHETIC ASSEMBLIES

(71) Applicant: The University of Iowa Research Foundation, Iowa City, IA (US)

(72) Inventors: Benjamin Dickerhoff, Coralville, IA (US); Robert S. Farivar, Minneapolis, MN (US); Madhavan L. Raghavan, Coralville, IA (US); Vijay Kumar, Iowa City, IA (US)

(73) Assignee: MEDICAL 21, INC., Plymouth, MN (US)

( * ) Notice: Subject to any disclaimer, the term of this patent is extended or adjusted under 35 U.S.C. 154(b) by 1256 days.

(21) Appl. No.: 16/787,291

(22) Filed: Feb. 11, 2020

(65) Prior Publication Data

US 2020/0170813 A1  Jun. 4, 2020

Related U.S. Application Data

(63) Continuation of application No. 14/377,086, filed as application No. PCT/US2013/025287 on Feb. 8, 2013, now abandoned.

(60) Provisional application No. 61/597,330, filed on Feb. 10, 2012.

(51) Int. Cl.
| | | |
|---|---|---|
| *A61F 2/24* | (2006.01) | |
| *A61F 2/86* | (2013.01) | |
| *A61F 2/95* | (2013.01) | |
| *A61L 27/20* | (2006.01) | |
| *A61L 27/50* | (2006.01) | |
| *B29C 39/02* | (2006.01) | |
| *B29C 39/10* | (2006.01) | |
| *C21D 1/18* | (2006.01) | |
| *C22F 1/10* | (2006.01) | |
| *A61F 2/07* | (2013.01) | |
| *B29K 1/00* | (2006.01) | |

(52) U.S. Cl.
CPC .............. *A61F 2/86* (2013.01); *A61F 2/2415* (2013.01); *A61F 2/95* (2013.01); *A61L 27/20* (2013.01); *A61L 27/507* (2013.01); *B29C 39/025* (2013.01); *B29C 39/10* (2013.01); *C21D 1/18* (2013.01); *C22F 1/10* (2013.01); *A61F 2/07* (2013.01); *A61F 2220/0025* (2013.01); *A61F 2240/001* (2013.01); *B29K 2001/00* (2013.01); *Y10T 29/49826* (2015.01)

(58) Field of Classification Search
CPC .................................................... A61F 2/2415
See application file for complete search history.

(56) References Cited

U.S. PATENT DOCUMENTS

| 7,481,835 B1* | 1/2009 | Pacetti | ................ A61L 31/16 |
| --- | --- | --- | --- |
| | | | 623/901 |
| 2002/0103526 A1* | 8/2002 | Steinke | ................ A61L 31/10 |
| | | | 623/1.11 |

(Continued)

FOREIGN PATENT DOCUMENTS

WO  2013119912  8/2013

OTHER PUBLICATIONS

International Search Report and Written Opinion issued in PCT/US2013/025287, dated Jun. 13, 2013.

*Primary Examiner* — Austin Murata
(74) *Attorney, Agent, or Firm* — Billion & Armitage

(57) ABSTRACT

Vascular prosthetic assemblies (e.g., heart valves), such as those, for example, configured to be deployed percutaneously.

3 Claims, 17 Drawing Sheets

(56) References Cited

U.S. PATENT DOCUMENTS

| | | | |
|---|---|---|---|
| 2002/0178570 A1* | 12/2002 | Sogard | A61F 2/07 29/516 |
| 2005/0096733 A1* | 5/2005 | Kovneristy | A61F 2/90 623/1.22 |
| 2006/0265053 A1 | 11/2006 | Hunt | |
| 2007/0038295 A1 | 2/2007 | Case | |
| 2007/0100432 A1 | 5/2007 | Case et al. | |
| 2008/0033522 A1 | 2/2008 | Grew et al. | |
| 2009/0222085 A1 | 9/2009 | Kumar | |
| 2010/0278893 A1 | 11/2010 | Bodin et al. | |
| 2012/0296418 A1* | 11/2012 | Bonyuet | A61F 2/2415 623/2.18 |

* cited by examiner

VASCULAR PROSTHETIC ASSEMBLIES

CROSS-REFERENCE TO RELATED APPLICATIONS

This application is a divisional of U.S. application Ser. No. 14/377,086, filed on Aug. 6, 2014, which is a national phase application under 35 U.S.C § 371 of International Patent Application Serial Number PCT/US13/25287, filed on Feb. 8, 2013, and which itself claims priority to U.S. Provisional Patent Application Ser. No. 61/597,330, filed Feb. 10, 2012, the entire disclosures of each of which are incorporated herein by reference.

FIELD OF THE INVENTION

The present invention relates generally to prosthetic assemblies (e.g., vascular) and, more particularly, but not by way of limitation, to heart valves and methods for using (e.g., percutaneously) and manufacturing (e.g., overmolding) the assemblies.

DESCRIPTION OF RELATED ART

An example of vascular prosthetic technology is disclosed in U.S. Patent Publication No. 2009/0222085 and U.S. Pat. No. 8,017,396, incorporated herein by reference. Further, examples of cellulose-based structures are disclosed in U.S. Pat. Nos. 6,800,753 and 8,017,396.

SUMMARY

This disclosure includes embodiments of vascular prosthetic assemblies (e.g., heart valves) and methods for using (e.g., percutaneously) and manufacturing (e.g., overmolding) the assemblies. In one embodiment, a vascular prosthetic assembly comprises a frame and a cellulose-based body coupled to the frame, wherein the frame is configured to be altered from an expanded configuration to a collapsed configuration. The frame can be biased toward the expanded configuration, and the assembly can be configured for placement within a catheter when the frame is in the collapsed configuration. In the embodiment shown, the frame can comprise any number of biocompatible materials, including, but not limited to, nitinol. stainless steel, or cobalt chromium. In the embodiment shown, the frame comprises a plurality of wires. The plurality of wires can be separate or linked. The frame may comprise a number of other wires, bars, linked wires, etc. to form the generally tubular shape.

In the embodiment shown, the cellulose-based body is generally tubular. In the embodiment shown, the cellulose-based body can be formed from any biocompatible cellulose-based mixture (e.g., a methylolcellulose solution, a silicone-cellulose solution, etc.). In one embodiment, the cellulose-based body is approximately 60 percent cellulose and 40 percent silicone by weight. In the embodiment shown, the cellulose-based body comprises a plurality of leaflets. The plurality of leaflets can move from an open configuration to a closed configuration. The plurality of leaflets can be configured to restrict a fluid flow through the assembly in the closed configuration.

In the embodiment shown, the assemblies can be configured for placement within a catheter to deploy the assemblies percutaneously in a heart. The catheter can be any size configured to deliver the assemblies to a heart annulus percutaneously (e.g., 5.0 mm, 7.0 mm, 9.0 mm, etc.). The assemblies can be sized similarly (e.g., between approximately 5.0 mm and 9.0 mm when the frame is in the collapsed configuration). One method of percutaneously deploying the assembly can comprise, inserting the assembly into a catheter, inserting the catheter into a native heart valve, deploying the assembly in the native heart valve, expanding the assembly, and retracting the catheter from the native heart valve. The method may further comprise inserting a guidewire through a vascular entry point to a region proximal to the native heart valve and inserting the catheter over the guidewire and into the native heart valve. In some embodiments, the method can further comprise inserting the guidewire through an aortic valve and into a left ventricle. In the embodiment shown, the frame is configured to remain in the expanded configuration when the assembly is deployed in a native heart valve. In other embodiments, the assembly may be deployed by any deployment method from the group consisting of transcatheter deployment, transapical deployment, retrograde vascular deployment, and antegrade vascular deployment.

The present invention also includes methods of manufacturing the present assemblies. In other embodiments the second diameter is smaller than the first diameter. In other embodiments, the generally tubular frame may be configured to have a first diameter configured for deployment in a heart. The method can further comprise pouring a volume of methylolcellulose solution over a mandrel, tilting (e.g., at an angle of approximately 45 degrees from vertical) and rotating the mandrel, submerging the mandrel in acetone and finally submerged in water or water-organic solvent to regenerate to cellulose. The generally tubular frame can comprise any number of biocompatible materials, including, but not limited to steel and nitinol.

In some embodiments, a method of manufacturing the present assemblies can comprise pouring a cellulose-based mixture over a mandrel to form a first cellulose-based layer, submerging the first cellulose-based layer in a first liquid, placing a generally tubular frame around the first cellulose-based layer, pouring the cellulose-based mixture over the generally tubular frame and the first cellulose-based layer to form a second cellulose-based layer, submerging the assembly in the first liquid (e.g., acetone), and submerging the assembly in a second liquid (e.g., water)

In some embodiments, a method of assembling a vascular prosthetic assembly can comprise providing a generally tubular frame comprising a plurality of apertures, coupling a cellulose body to the generally tubular frame wherein the cellulose body is disposed within a lumen of the generally tubular frame and wherein the cellulose body extends through the plurality of apertures to form a plurality of loops, inserting a bar into each loop formed by the cellulose body extending through generally tubular frame, and securing each bar to the generally tubular frame.

In certain embodiments, each bar can comprise a hook on one end. In particular embodiments, the bar can be configured as a wire. In specific embodiments, the plurality of apertures can be configured as elongated gaps spaced around the circumference of the generally tubular frame. In particular embodiments, each bar can be secured to the generally tubular frame with sutures. Certain embodiments can further comprise cutting the length of the cellulose body.

Specific embodiments can further comprise coupling struts to the generally tubular frame to reinforce the plurality of apertures.

Any embodiment of any of the present apparatuses can consist of or consist essentially of—rather than comprise/include/contain/have—any of the described elements and/or features. The same is true of the present methods. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The embodiments of the present cellulose-based prosthetic assemblies and their components shown in the figures are shown to scale for at least the depicted embodiment.

DESCRIPTION OF ILLUSTRATIVE EMBODIMENTS

Figure 1:
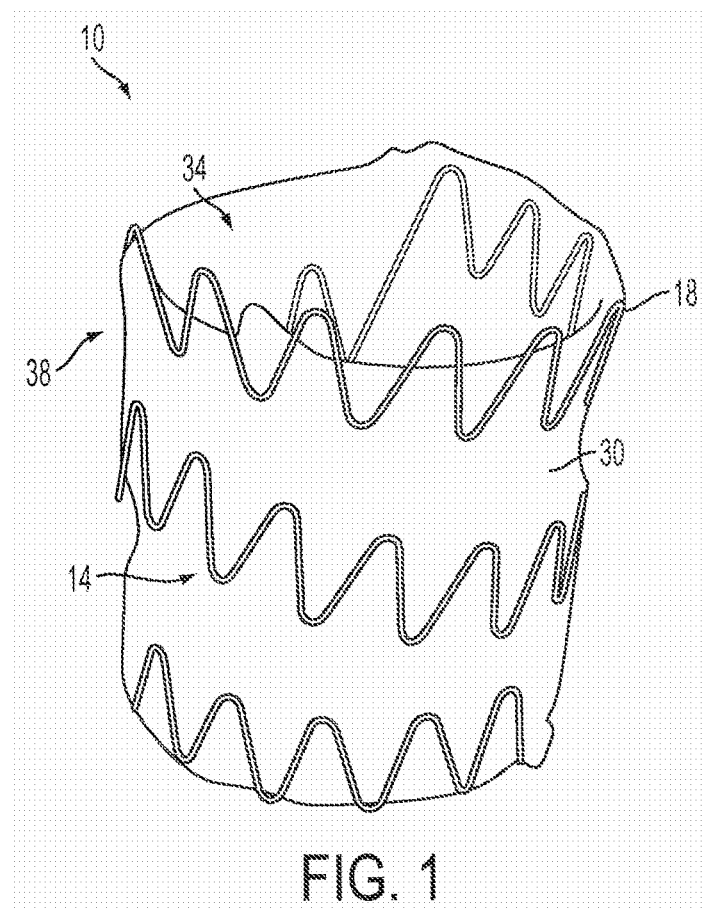
FIG. 1 depicts a perspective view of one embodiment of the present assemblies having a separated tubular frame and a body.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The terms "substantially" and "generally" are defined as largely but not necessarily wholly what is specified (and includes what is specified; e.g., substantially 90 degrees includes 90 degrees and generally parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, a vascular prosthetic assembly, or a component of such an assembly, that is configured in a certain way is configured in at least that way, but it can also be configured in other ways than those specifically described.

1. GENERAL OVERVIEW

Vascular prosthetic assemblies can include, for example, animal valves and pericardial tissue sutured to a stent frame. Animal and prosthetic valves can be implanted in various ways, including, surgically and percutaneously. Some mechanical or bioprosthetic assemblies can be surgically sutured at the location of a diseased valve. These prosthetic assemblies can be compromised by calcification of leaflets (e.g., with a bioprosthetic fixed with a chemical preservative). Further, surgical implantation can require anesthetizing and intubating a patient, as well as placing a patient on cardiopulmonary bypass. Recovery could require 5-7 days in a hospital and an additional 4-6 weeks at home. Additionally, surgical implantation may only be recommended for approximately 80 percent of patients. Those that may not be recommended for a surgical implantation (e.g., elderly individuals, individuals with a Society of Thoracic Surgeons (STS) risk of >10% mortality, etc.) could have as small as a 50 percent survival rate at two years and a 20 percent survival rate at five years. Additionally, anticoagulation therapy can be needed.

Embodiments of the present invention can be implanted surgically or delivered percutaneously. Percutaneous (e.g., transcatheter) implantation of vascular repair assemblies is an alternative to surgery. Percutaneous valves currently approved for select patients can be manufactured using animal tissue (e.g., pig, cow, horse, etc.). These bioprosthetic valves can be preserved using glutaraldehyde to enhance its mechanical stability; however, this preservative could result in bioprosthetic deterioration from calcification.

2. STRUCTURAL OVERVIEW

Embodiments of the present assemblies can be configured to act as, for example, vascular repair devices, scaffolding to cultivate tissue-engineered valves, permanent stent grafts, and the like. More specifically, the present assemblies can act as prosthetic heart valves. The assemblies can be implanted, for example, surgically or percutaneously. FIGS. 1-5 depict embodiments of the present assemblies 10. Assemblies 10 comprise a frame 14 (e.g., a stent). Frame 14 can comprise a plurality of (e.g., two, three, or more) wires 18 disposed in various configurations. In some embodiments, plurality of wires 18 can be unitary. In the embodiment shown, frame 14 is substantially tubular (e.g., cylindrical). In some embodiments, frame 14 can comprise a substantially similar shape to the device with which it is delivered. In other embodiments, frame 14 can comprise a substantially similar shape to the location in which it is deployed.

As depicted in FIG. 1, for example, each of a plurality of wires 18 can be substantially wave-like. In other embodiments, wires 18 can take any shape configured to allow for percutaneous delivery (discussed in detail below). To form frame 14, plurality of wires 18 can be separate (e.g., FIGS. 1, 4B, and 4C) or linked (e.g., a series of repeating diamonds as in FIGS. 2A, 3B, and 3C). The shape of plurality of wires 18 can be formed in a number of ways, including, but not limited to, bending the wire and/or laser cutting the wire to remove a desired pattern from a solid tube.

Figure 2A:
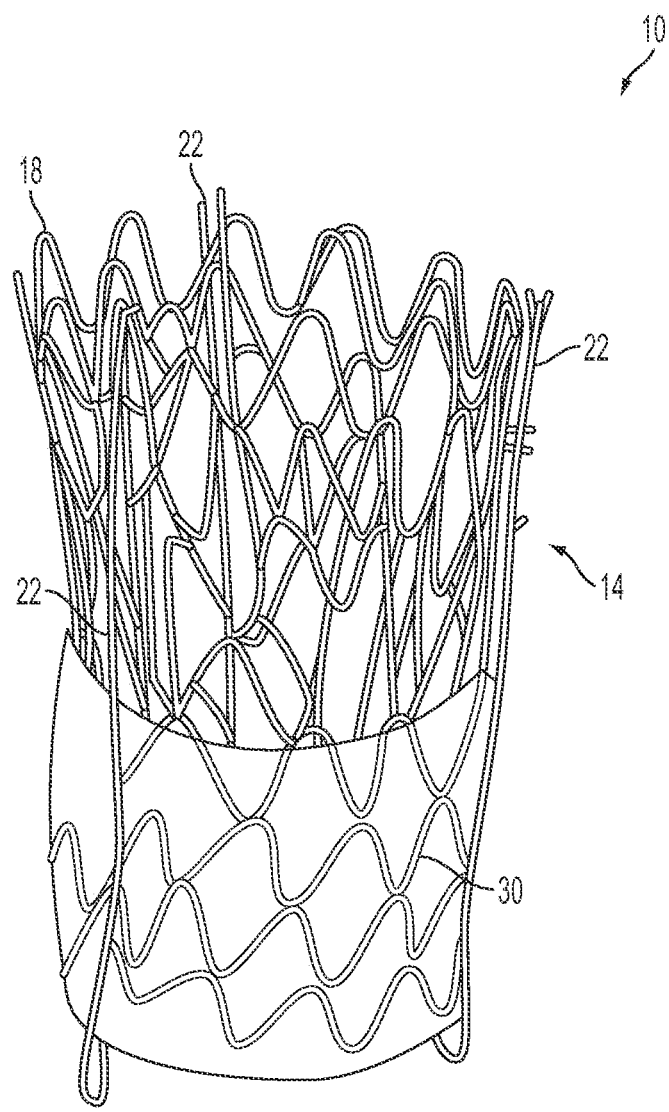
FIG. 2A depicts a perspective view of one embodiment of the present assemblies having a linked tubular frame partially covered by a body.
Figure 2B:
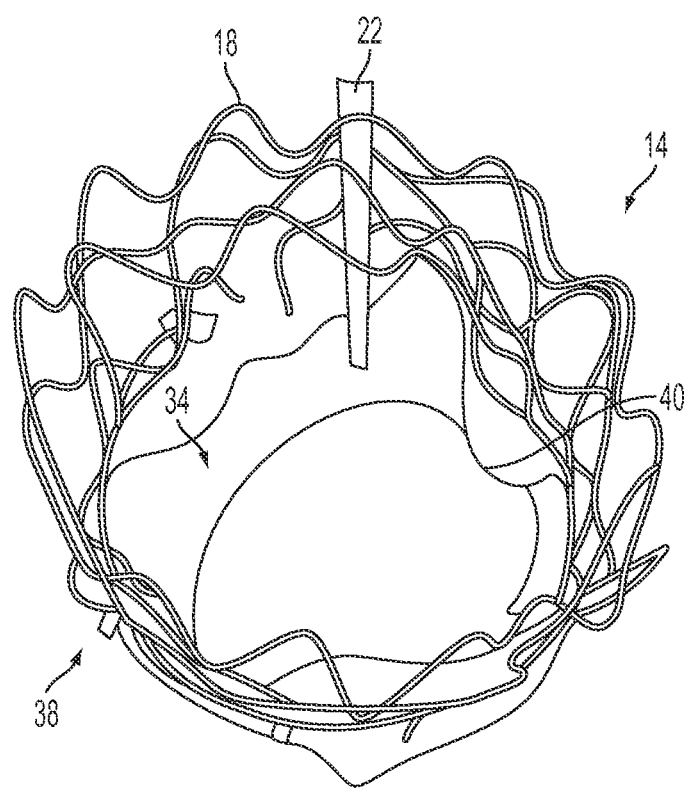
FIG. 2B depicts a top view of the assembly in FIG. 2A.
Figure 2C:
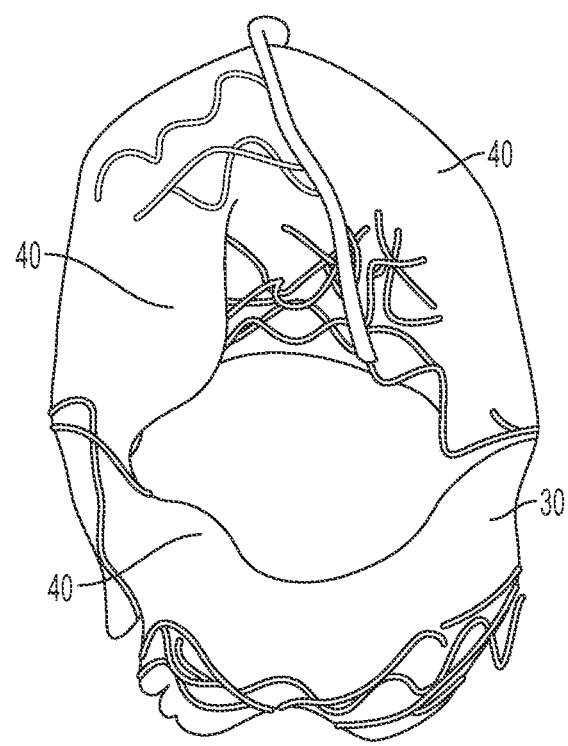
FIG. 2C depicts a bottom view of the assembly in FIG. 2A.
Figure 3A:
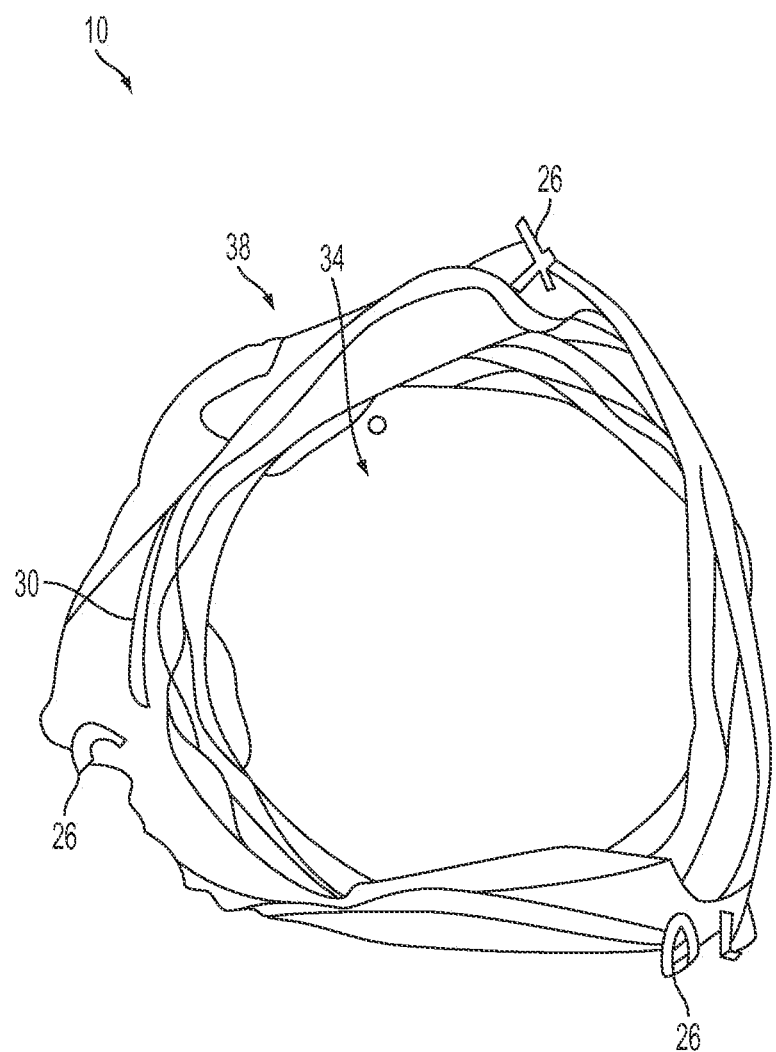
FIG. 3A depicts a top view of the present assemblies having a linked tubular frame with linking wires extending vertically from the frame and a body.
Figure 3B:
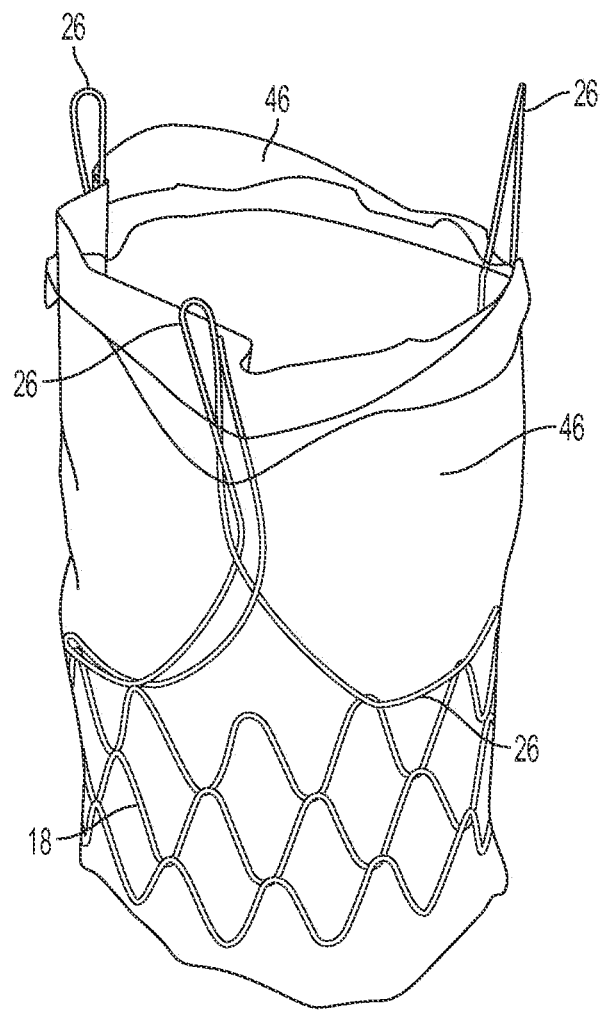
FIG. 3B depicts a perspective view of the assembly in FIG. 3A.
Figure 3C:
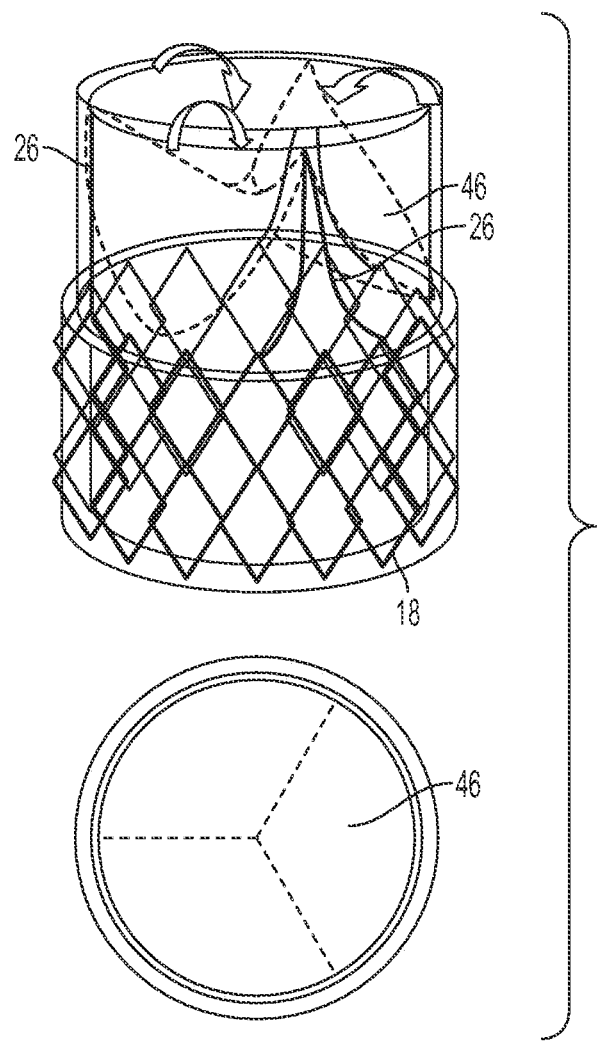
FIG. 3C depicts a graphical representation of the assembly in FIG. 3A from a side view and a top view.

In some embodiments, as depicted in FIG. 2A-2C, frame 14 comprises wires 18 and one or more vertical bars 22. In the embodiment shown, bars 22 are disposed substantially perpendicular to wires 18. Bars 22 can be—but are not required to be—spaced equally along the circumference of assembly 10. In other embodiments, as depicted in FIGS. 3A-3C, frame 14 can be comprised of linking wires 26. Portions of linking wires 26 can be coupled to wires 18. Further, portions of linking wires 26 can be disposed vertically such that portions of linking wires 26 are substantially perpendicular to wires 18 (e.g., similarly to bars 22). In some embodiments, wires 18, bars 22, and/or linking wires 26 can be unitary.

Frame 14 can be constructed from any biocompatible material that can withstand significant deformation without compromising rigidity. These materials include, for example, nitinol and/or stainless steel. The radially collapsible frame can provide structural rigidity to assembly 10.

Figure 2D:
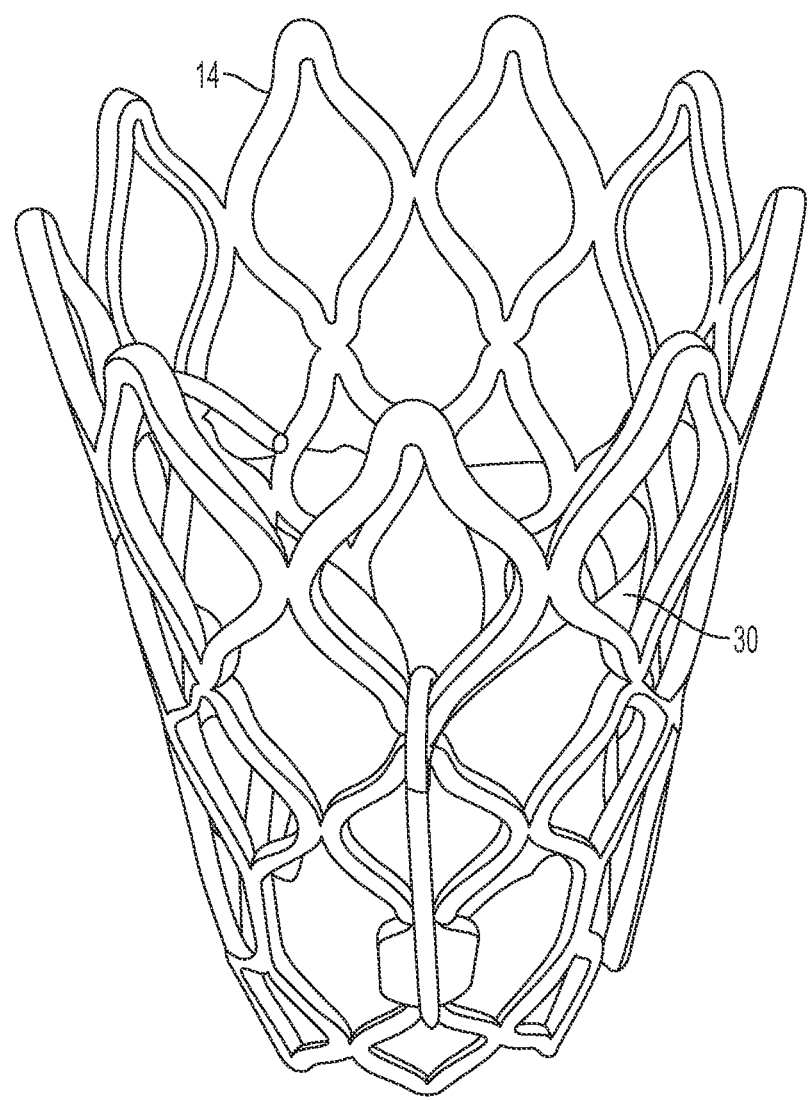
FIG. 2D depicts a perspective view of one embodiment of the present assemblies having a linked tubular frame with a body inserted.

In the embodiment shown, a body 30 is coupled to frame 14. In the embodiment shown, body 30 may extend the full length of frame 14 (e.g., FIGS. 1 and 4B) or a partial length of frame 14 (e.g., FIG. 2A). Body 30 can be coupled to inner portion 34 of frame 14 (e.g., FIG. 1), outer portion 38 of frame 14 (e.g., FIG. 2A), or both inner and outer portions 34 and 38 of frame 14 (e.g., FIG. 3A). Free edges 40 of body 30 can touch to form areas of coaptation (e.g., FIGS. 1 and 2A-2C) and/or be secured along the circumference of frame 14. FIG. 2D illustrates an embodiment in which frame 14 is formed as a single continuous unite (e.g. through laser cutting) rather than multiple components sutured together.

In the embodiment shown, body 30 can comprise one or more leaflets 46. As depicted, for example, in FIGS. 3B, 3C, 4A, and 4C, leaflets 46 can extend from body 30 toward a centerpoint of assembly 10. In some embodiments, free edges 40 can form leaflets 46. Leaflets 46 can meet such that the intersection of leaflets 46 resembles the geometry of a human heart valve. In other embodiments, leaflets 46 can be configured to resemble any location in which assembly 10 is deployed. In the embodiment shown, leaflets 46 can be configured to move assembly 10 between an open and a closed configuration. Leaflets 46 can further be configured to restrict fluid flow through assembly 10 when assembly 10 is in a closed configuration. In some embodiments, leaflets 46 can remain in a closed configuration until a fluid flow forces leaflets 46 apart (e.g., creating an open configuration). In other embodiments, the preferred configuration of assembly 10 is an open or semi-open configuration (e.g., with leaflets 46 open or semi-open as in shown, for example, in FIG. 3B). For example, in some embodiments (e.g., FIGS. 2A-2C), leaflets 46 can be forced to the interior wall of frame 14 in an open configuration (e.g., when fluid passes through assembly 10). When the fluid flow begins to reverse, leaflets 46 can coapt to form a seal. In some embodiments (e.g., FIGS. 3B and 3C), leaflets 46 of body 30 are configured to fold inward between bars 26 such that assembly 10 can be in a closed configuration.

Body 30 can be cellulose-based (e.g., pure cellulose, cellulose-silicone mixture, etc.). Cellulose-based bodies can be naturally-occurring, biocompatible, biostable, and/or flexible. Further, cellulose-based bodies can be highly optimizable (e.g., in geometry, porosity, surface adhesion characteristics, mechanical properties, hemodynamic properties, biocompatibility, wall thickness, etc.).

In the embodiment shown, assemblies 10 can be configured to be delivered (e.g., via peripheral vessels) by a catheter (e.g., a small femoral and/or transapical sheath, etc.) and/or a similar delivery device. In some embodiments, assemblies 10 can be delivered by any number of methods, including, but not limited to transcatheter deployment, transapical deployment, retrograde vascular deployment, and/or antegrade vascular deployment. Frame 14 and body 30 can be configured to be altered from an expanded configuration to a collapsed configuration, with frame 14 biased toward the expanded configuration. In other embodiments, frame 14 can be biased toward a collapsed configuration. In the embodiment shown, assembly 10 is configured for placement within a catheter when frame 14 is in the collapsed configuration. Frame 14 can be configured to provide sufficient radial (e.g., outward) force such that migration is prevented (e.g., when deployed in a heart annulus). Frame 14 can allow for radial compression into a catheter sheath while still providing structural rigidity to hold assembly 10 fixed in position after being deployed. Assembly 10 can be configured for placement within a catheter having an outer diameter of approximately 7.0 mm when frame 14 is in the collapsed configuration. Assembly 10 can further be configured for placement within a catheter having an outer diameter of between approximately 4.0 mm and 9.0 mm (or smaller in some embodiments) when frame 14 is in the collapsed configuration. In other embodiments, assembly 10 can be sized for placement within any catheter capable of delivering a prosthetic assembly to the heart percutaneously.

As discussed above, assembly 10 can be deployed surgically or percutaneously. In the embodiment shown, assembly 10 can be configured to be deployed percutaneously. One method to deploy assembly 10 percutaneously comprises (1) inserting assembly 10 comprising frame 14 and body 30 into a catheter; (2) inserting the catheter into a native heart valve; (3) deploying assembly 10 into the native heart valve; (4) expanding assembly 10; and (5) retracting the catheter from the native heart valve. This method can further comprise inserting a guidewire through a vascular entry point (e.g., the femoral artery) to a region proximal to the native heart valve (e.g., through an aortic valve and into a left ventricle) and inserting the catheter over the guidewire and into the native heart valve. The guidewire can be removed once assembly 10 is deployed.

Assemblies 10 can be constructed in various ways. One such method comprises overmolding in which body 30 is molded around frame 14. Overmolding can be an alternative to binding body 30 to frame 14 with sutures. This method of manufacturing assembly 10 can comprise: (1) configuring a generally tubular frame 14 to have a first diameter configured for deployment in the native heart valve; (2) heating generally tubular frame 14; (3) quenching generally tubular frame 14 in liquid; (4) configuring generally tubular frame 14 to have a second diameter larger than the first diameter; (5) cooling generally tubular frame 14; (6) forming solidified methylolcellulose matrix; (7) allowing stent frame to warm and consequently shrink to the solidified methylolcellulose matrix; (8) coupling outer layer of solidified methylolcellulose matrix to inner layer; and (9) submersing in water to create cellulose body 30 containing stent frame 14. In order to overmold the stent frame within the cellulose membrane, an initial layer of solidified methylolcellulose matrix is created in tubular form on a separate mandrel from the stent. This is done by submersing a cylindrical mandrel with an even coat of methylolcellulose solution surrounding it into acetone or alcohol. The stent frame is placed on a mandrel slightly larger than the mandrel with the solidified methylolcellulose matrix and cooled. Cooling the stent frame temporarily holds it in a configuration that allows it to fit onto the initial layer of solidified methylolcellulose matrix without causing damage. As the stent frame warms up, it returns to its heat treated configuration and fits snuggly up against the initial layer of solidified matrix. Methylolcellulose solution is then poured over the stent frame and the initial solidified methylolcellulose matrix before submersing in acetone to create an outer coating. This outer coating fuses with the initial coating and couples the stent frame within the solidified matrix. The cellulose-based body is regenerated once the solidified methylolcellulose matrix body has been submersed in water. In other embodiments, frame 14 may have a first diameter that is configured for deployment in a heart and a second diameter that is configured for placement within a catheter. In some embodiments, frame 14 can be steel. The overmolding method listed above is slightly different when using an stent material other than nitinol. Specifically, the stent formation is formed by mechanically displacing the stent frame radially until the desired expanded diameter is achieved. Cooling is not necessary to hold it in the diameter just beyond the expanded diameter. Mechanical compression is used to press it radially inwards to compress onto initial solidified methylolcellulose matrix.

The method can further comprise configuring generally tubular frame 14 to have a first diameter by inserting frame 14 into a fixture and/or disposing frame 14 around a mandrel. For example, frame 14 (e.g., comprising a nitinol material) can be firmly constrained in a fixture and/or around a mandrel in a configuration suitable for percutaneous deployment (e.g., via a catheter). Frame 14 can be heat treated at a high temperature to alter the physical properties of the material of frame 14. Frame 14 can then be quenched in water to permanently set its shape. Frame 14 can next be stretched over a mandrel with a diameter slightly larger than the mandrel used to create body 30 (discussed in detail below). Frame 14 can then be cooled.

Body 30 can be constructed in various ways. For example, constructing body 30 can comprise pouring a volume of solution (e.g., methylol cellulose solution) over a mandrel (e.g., creating an even coat around the mandrel). Thickness of body 30 can be varied based on the volume of solution poured on the mandrel. The mandrel can be tilted (e.g., at approximately 45 degrees from vertical) and rotated. Body 30 can then be submersed in water, acetone, and the like to begin regeneration. This method can create a single body 30 that has the effect of comprising separate leaflets 46. In another embodiment, a methylolcellulose solution is poured over a rotating mandrel with spacers at both ends of the mandrel set at a desired thickness. As the mandrel is rotating, a sheet with a straight edge is placed on top of the spacers, and any material beyond the desired thickness is removed.

Body 30 can also be formed, for example, by pouring a solution (e.g., a methylolcellulose solution) into a mold resembling an aortic valve in a closed state. Two mold halves can be used to form a uniform leaflet thickness and surface quality. One half of the mold can resemble a closed human heart valve with respect to the left ventricle toward the aortic arch. The other half can be the inverse of the first half (e.g., resembling an aortic valve in a closed position with respect to the aortic arch toward the left ventricle). Body 30 can optionally be submerged into a bath of liquid (e.g., DMSO-miscible organic solvent and/or any mixed solvent suitable to form a solid methylolcellulose matrix). Body 30 can be fully regenerated to a cellulose-based structure by submerging body 30 in a bath of water. Frame 14 can then be set interior to or exterior to body 30 or within.

In other embodiments, for example, as depicted in FIGS. 2A-2C, assembly 10 can be constructed by pouring a cellulose-based solution (e.g., a methylolcellulose solution) over a rotating mandrel such that an even layer of cellulose-based solution covers the mandrel to form a first layer of body 30. The methylol-cellulose solution can be solidified by submerging the covered mandrel into acetone. Frame 14 can be slightly expanded radially and placed over the temporarily solidified cellulose-based body 30. As shown in FIGS. 2A-2C, a bottom portion of frame 14 can overlap cellulose-based body 30 and a top portion of frame 14 may not be in contact body 30. A portion of body 30 can extend beyond the bottom portion of frame 14 to form leaflets 46. To overmold assembly 10, additional layers of cellulose-based solution can be poured over frame 14 and the first layer of body 30. Cellulose-based body 30 can be solidified between layers by submerging assembly 10 in acetone. A final layer of cellulose-based solution can be added, and overmolded assembly 10 can be submerged into a bath of water to regenerate the cellulose-based solution to cellulose. Cellulose body 30 that extends beyond the bottom portion of frame 14 can be folded into overmolded frame 14 to form leaflets 46. Three clips can be—but are not required to be—placed an equal distance apart on the circumference of frame 14 to secure body 30 (e.g., such that the clips can represent heart valve commissures).

In some embodiments, assembly 10 can mold body 30 to inner and outer portions 34 and 38 of frame 14 using a tilted mandrel. A volume of solution (e.g., methylolcellulose solution) can be poured over a cylindrical mandrel. The mandrel can be tilted (e.g., at a 45 degree angle) and rotated until obtaining a desired leaflet thickness to be disposed in inner portion 34. The coated mandrel can then be submerged in acetone to create a solidified methylolcellulose matrix. A cooled frame 14 (e.g., using the technique described above) can be placed over the mandrel containing leaflet 46 constructed for inner portion 34. Cooling frame 14 allows frame 14 to maintain a rigid shape while it is placed over a leaflet to prevent damage. A volume of solution (e.g., methylolcellulose solution) can be poured over the mandrel containing frame 14 and leaflet 46 constructed for inner portion 34. The mandrel can then be tilted (e.g., at a 45 degree angle from vertical) and allowed to rotate until reaching a desired thickness. The mandrel can then be placed into a vacuum chamber to remove air bubbles within leaflet 46. Frame 14 and leaflet 46 can then be submerged into acetone to generate a solidified methylolcellulose matrix. Once removed from the acetone, leaflet 46 constructed for outer portion 38 can be formed by pouring a volume of solution (e.g., methylolcellulose solution) over frame 14 and leaflet 46 constructed for inner portion 34 that are located on the mandrel. The mandrel can then be tilted (e.g., at a 45 degree angle) and allowed to rotate until reaching the desired thickness. The coated mandrel can be submerged in acetone to solidify the methylol-cellulose and to achieve a smooth surface quality. The assembly can finally be submerged in water until fully regenerated.

Overmolding can also be used in other applications. For example, overmolding can be used to overmold fibers within leaflets 46 for structural support (e.g., similarly to native human aortic valves that have anisotropic mechanical properties with a stiffer circumferential direction helping to resist tearing as the leaflet flexes during opening and closing). Further, overmolding can be used to create an anisotropic material by positioning stiffer fibers oriented in a circumferential direction between layers of leaflets 46.

Body 30 can be constructed using various materials. Body 30 can comprise pure (e.g., about 100%) cellulose material. Body 30 can also comprise a cellulose-silicone composite and/or any other composite comprising similar material properties. A cellulose-silicone composite can be created similarly to a pure cellulose membrane. In certain embodiments, a platinum-catalyzed silicone can be prepared by mixing a silicone base with an activator (other embodiments may utilize different types of silicone). It can be mixed, for example, in a 10:1 silicone base to activator ratio by weight. The platinum-catalyzed silicone mixture can begin to cure and solidify shortly after mixture. The silicone can be placed into a vacuum chamber to be degassed. Silicone can then be poured into a glass container with methylolcellulose solution (e.g., in the desired ratio of cellulose to silicone by mass). The solution can be mechanically stirred for a period of time long enough to ensure thorough distribution of silicone within the solution. The mixture of cellulose and silicone can be placed into a vacuum chamber to be degassed. The mixture can then be molded and set. After the set time, the mold can be submerged into water to regenerate the cellulose. The composite mixture can also be submerged prior to the silicone set time.

In certain embodiments, body 30 may comprise a bacterial cellulose material rather than (or in addition to) the regenerated cellulose material described above. In specific embodiments, the bacterial cellulose is a byproduct of the metabolic process of certain strains of bacteria, forming a protective envelope around the cells in the presence of oxygen and glucose. Bacterial cellulose can be particularly suited for applications such as body 30 due to its chemical purity, strength, moldability, and increased water retention ability.

In addition, bacterial cellulose is chemically equivalent to regenerated plant cellulose, but includes a unique macromolecular structure and associated properties as compared to plant cellulose. In particular embodiments, interwoven ribbons (e.g., 20-100 nanometers wide in some applications) of cellulose fibrils (2-4 nm wide) constitute the bacterial cellulose pellicle. This structure can be particularly suited for cardiovascular applications. For example, the formation of fibers provides it an underlying structural reinforcement, not unlike natural valve tissue, that can increase its failure strength without significantly impacting its flexibility, as well as improve resistance to tearing and consequently, durability.

In particular embodiments, the bacterial cellulose of body 30 may be produced by utilizing the *Gluconacetobacter xylinus* (ATCC 10245) strain of bacteria cultured statically in Hestrin-Schramm medium to obtain pellicles of bacterial cellulose. One factor in the formation of a bacterial cellulose pellicle is the location in which the culture medium is exposed to air. For example, if a beaker partially filled with culture medium was left uncovered, the pellicle can form as a flat circular sheet covering the surface of the medium. In the same way, a specific bacterial cellulose pellicle geometry can be achieved by designing a mold permeable to air in a desired shape.

For example, one such geometry is a tubular configuration. In a specific embodiment shown in FIG. 4D, a tubular apparatus made of a thin permeable silicone tube 100 can be submerged in container 110 containing Hestrin-Schramm medium cultured with the strain of cellulose producing bacteria. Tube 100 can be capped off at the far end of the tube with a stopper 120 so no air can escape out of the bottom, and the top of tube 100 can be plugged with a two-holed rubber stopper 130. An air source can then be used to pressurize the silicone tube via a first hole 132 in stopper 130 to sufficiently to maintain its patency. A second hole 134 can be constricted to allow for a controlled release of air and the cellulose pellicle can form as a tube (e.g. on the outside of tube 100) at the interface where the air is allowed to permeate through the thin silicone wall. Once the desired thickness has been reached, the cellulose pellicle can be rinsed and sterilized. In specific embodiments, the desired thickness can be established based on visual observation and/or the amount of time that the cellulose pellicle is allowed to form. In one particular embodiment, the cellulose pellicle is allowed to form for approximately six days in order to obtain the desired thickness.

Several methods can be used to attach body 30 (comprising either regenerated plant cellulose or bacterial cellulose) to frame 14. For example, overmolding (as described above) can be used with some modifications—specifically, a stent frame is placed onto the forming cellulose pellicle as it continues to grow, enveloping it within the matrix of cellulose fibers. Alternatively, sutures can be used to adhere body 30 to frame 14. In addition, portions of body 30 can be pinched between one or more portions of frame 14 (e.g., when frame 14 comprises linked wires 18 as depicted, for example, in FIGS. 2A, 3B, and 3C). In one specific embodiment shown in FIG. 4E, after formation, the newly formed cellulose tube for body 30 is attached to stent frame 14. The tube can be trimmed to a desired length with clean edges and placed in the lumen 7 of stent frame 14. In the embodiment shown, stent frame 14 has a plurality of apertures 13 around the circumference of the frame at the locations where the commissures are to form. In the specific embodiment shown, apertures 13 may be formed as long narrow gaps spaced equally around the circumference.

Figure 4A:
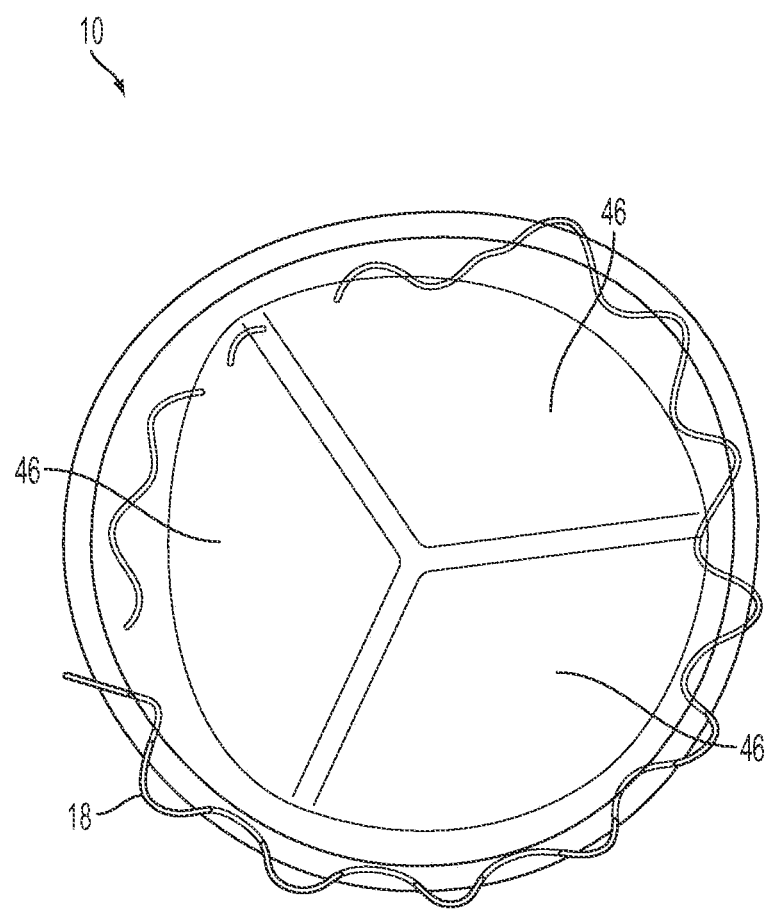
FIG. 4A depicts a top view of the present assemblies having a separated tubular frame and a body comprising.
Figure 4B:
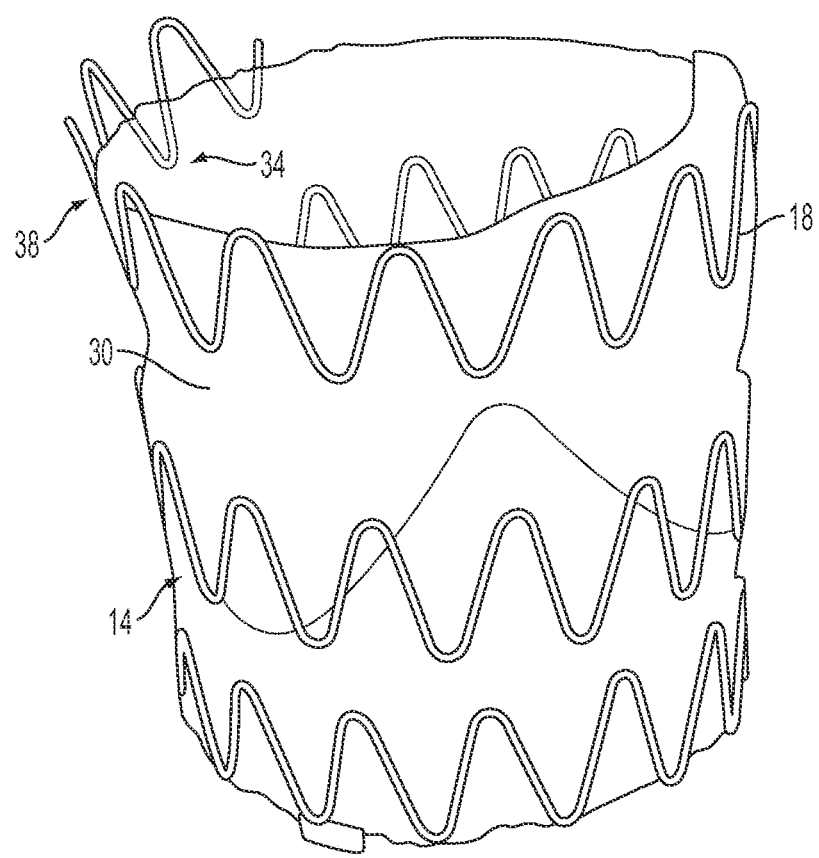
FIG. 4B depicts a perspective view of the assembly in FIG. 4A.
Figure 4C:
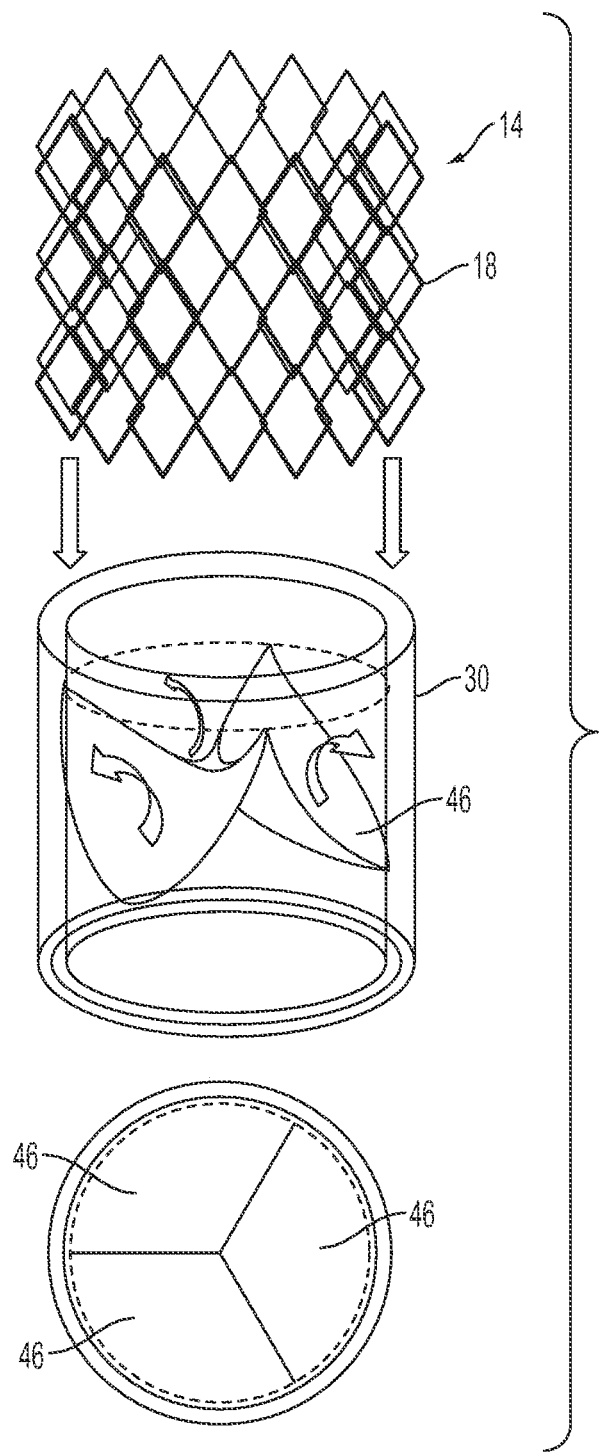
FIG. 4C depicts a graphical representation of the assembly in FIG. 4A from a side view and a top view.
Figure 4D:
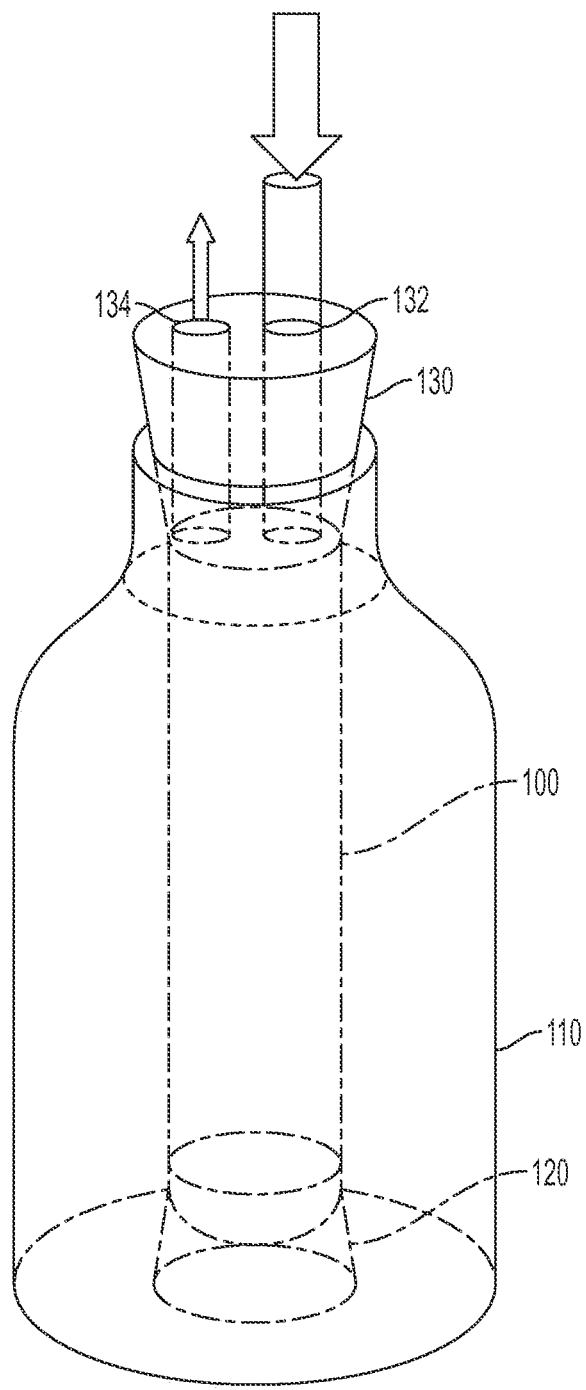
FIG. 4D depicts an apparatus used to form a body.
Figure 4E:
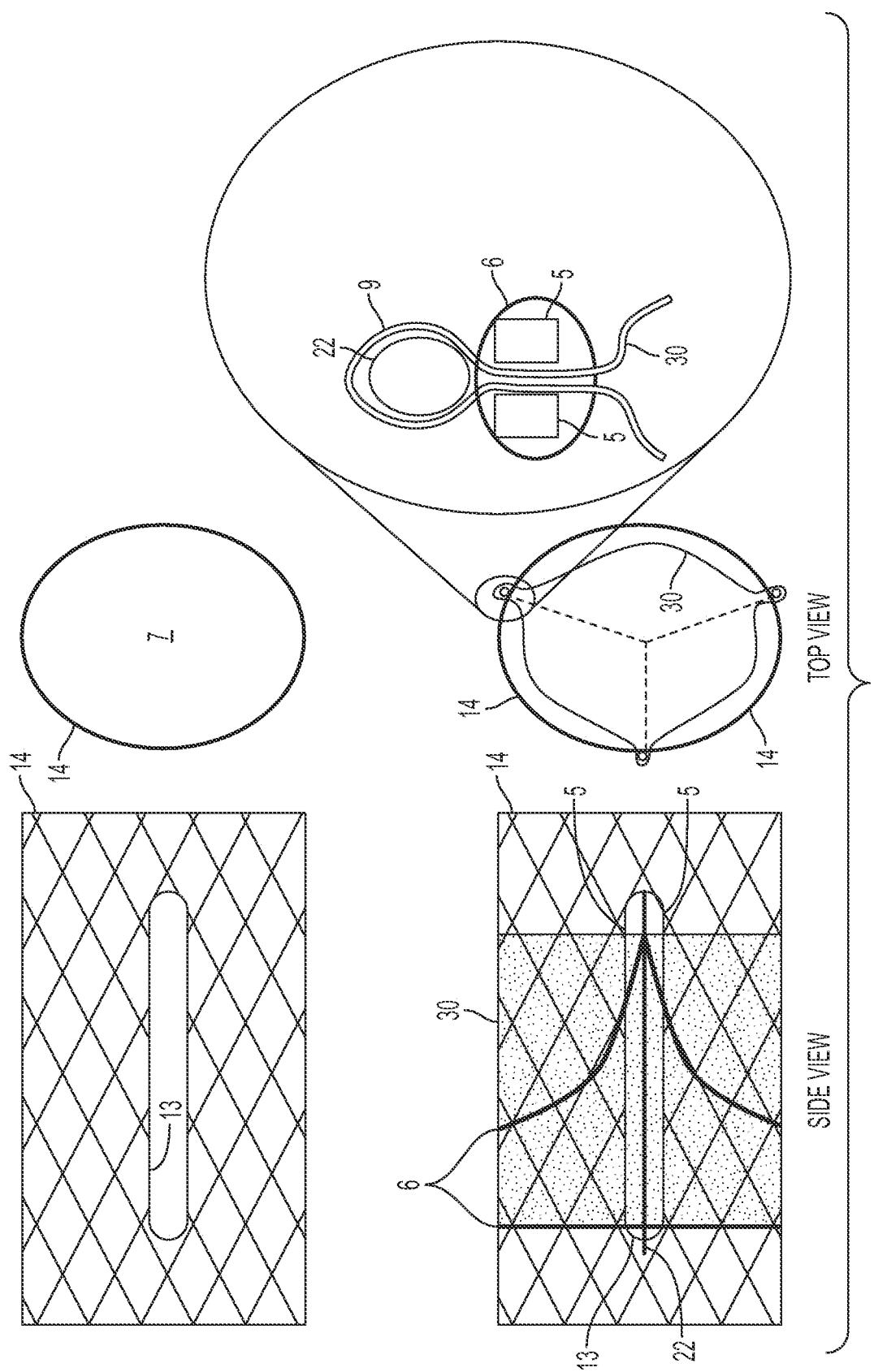
FIG. 4E depicts a graphical representation of an alternative method for assembly from a side view and a top view.

In this embodiment, body 30 is pinched and slid in between apertures 13 of stent frame 14 and pulled towards the outside of stent frame 14. As shown in FIG. 4E, the section of body outside the stent frame has formed a loop 9. A bar 22 can be inserted in loop 9 and secured to stent frame 14. In certain embodiments, bar 22 can be configured as a stiff, straight wire slightly longer than aperture 13. In this embodiment, bar 22 can be used to secure body 30 from slipping back through aperture 13. Body 30 can then be pulled taught towards lumen 7 of stent frame 14. In the embodiment shown, sutures 6 are threaded around the outside of aperture 13 and pulled taught, effectively pinching the membrane between a pair of struts 5 next to each aperture 13 that can serve to reinforce aperture 13. In this exemplary embodiment, the lower edge of body 30 is also sutured around stent frame 14 and a U-shaped pattern is sutured around the circumference of the stent frame between the bars 22.

Figure 5:
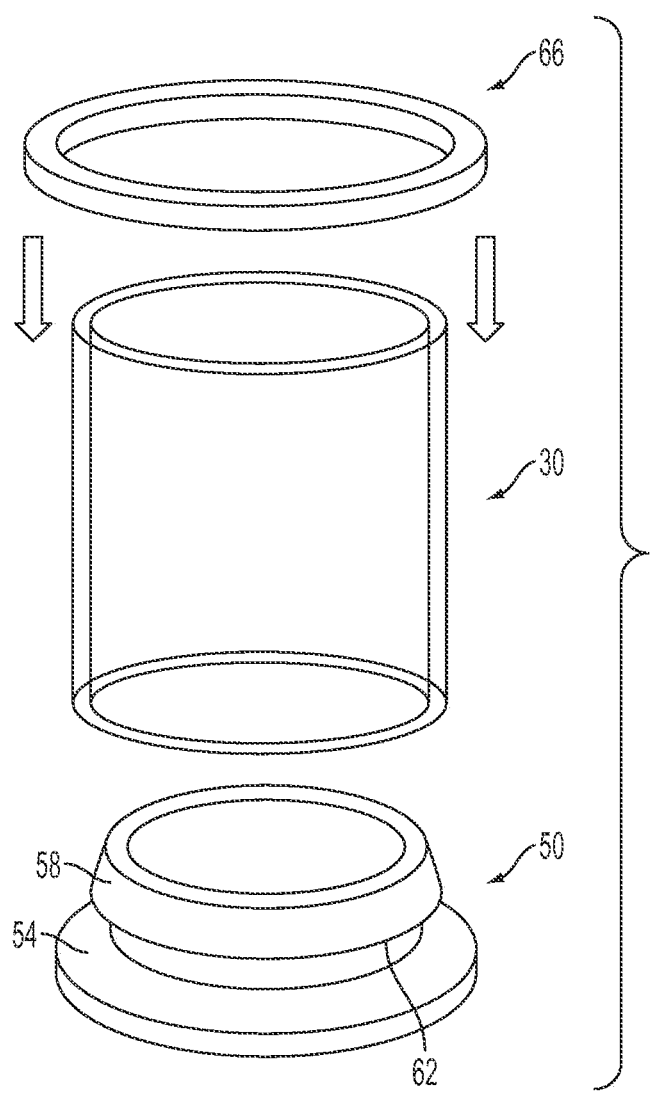
FIG. 5 depicts a graphical representation of one method of attaching a body to a frame using a press-fit mechanism.

Further, as depicted in FIG. 5, a press-fit mechanism can be used to secure body 30 to frame 14. For example, one end of body 30 can be stretched over a bottom portion 50 of frame 14. In the embodiment shown, bottom portion 50 can comprise a ring 54 and a nozzle 58. Nozzle 58 can comprise a lip 62 to assist in securing body 30. In some embodiments, bottom portion 50 of frame 14 can comprise any number of components and/or shapes to assist in securing body 30 to frame 14. In the embodiment shown, the press-fit mechanism comprises an upper portion 66. Upper portion 66 can comprise a shape inverse to bottom portion 50 such that upper portion 66 can fit securely with bottom portion 50. In the embodiment shown, a lower portion of body 30 can be disposed between bottom portion 50 and upper portion 66 such that the lower portion of body 30 cannot move freely of bottom portion 50 and upper portion 66. The remainder of frame 14 and body 30 can comprise a shape similar to the embodiments depicted in FIGS. 1-5. In other embodiments, body 30 is attached to frame 14 by commisure posts. Commisure posts can comprise, for example, a plurality of clips that are—but are not required to be—spaced equally around the circumference of body 30 and frame 14.

3. EXAMPLES

Figure 6:
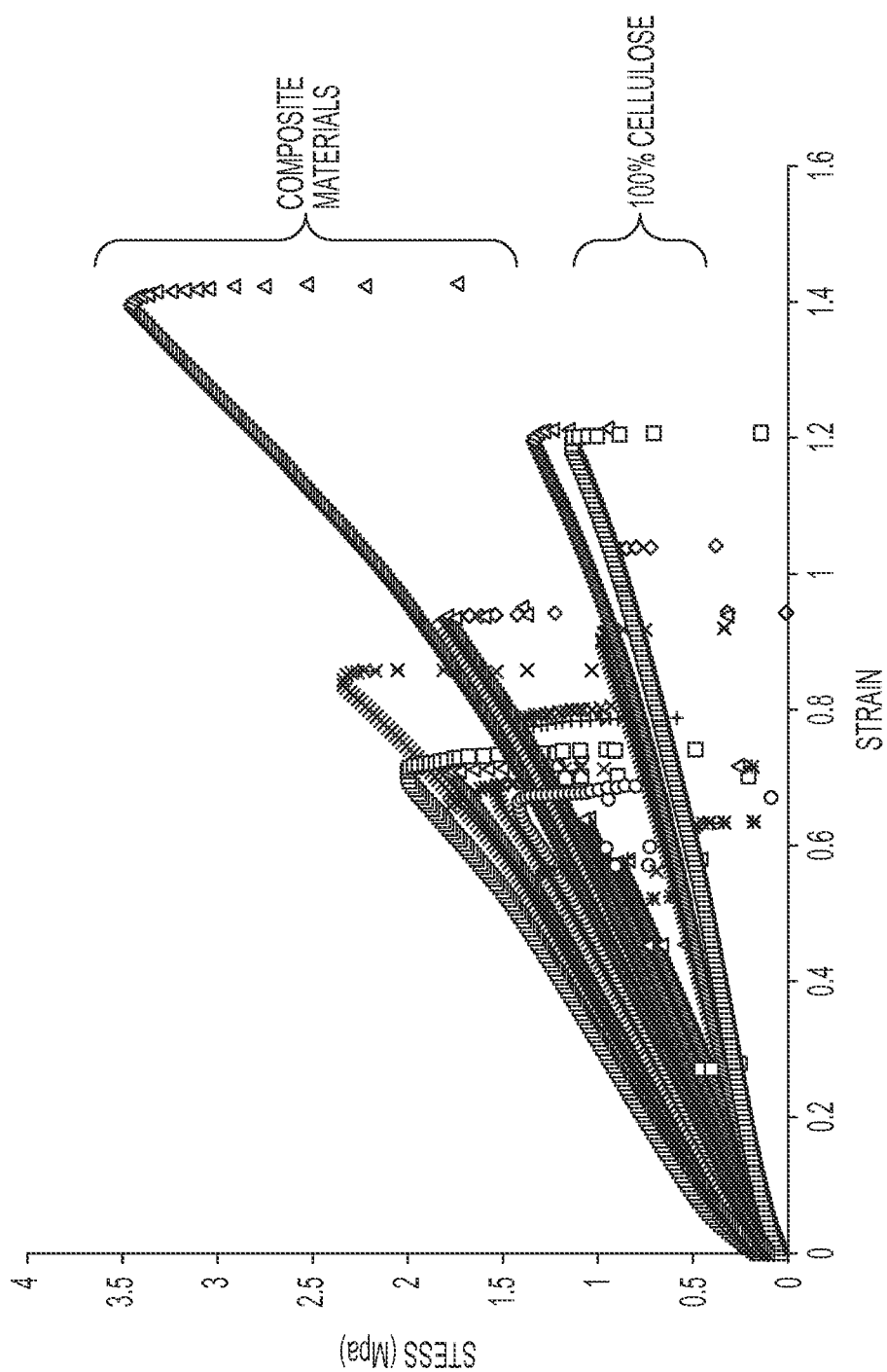
FIG. 6 depicts a stress-strain curve for pure cellulose bodies and cellulose-silicone bodies.

Tests were performed on an embodiment of the present invention to observe its properties. Cellulose-based membranes were uni-axial extension tested to collect stress-strain data (depicted graphically in FIG. 6). This assessed the ability of assemblies to substitute as a native aortic valve. The results from the stress-strain tests were compared to values reported for human aortic valve samples. The results (see TABLE 1) indicated that the cellulose-based material can be a plausible alternative to replace a damaged aortic valve. The cellulose-based material exhibited a more linear and isotropic response to stress than a normal aortic valve. The cellulose-based material's modulus of elasticity was comparable to reported values of human valve leaflet samples cut in the radial direction. The ultimate stress value was also within the values reported for normal aortic valve tissue. The ultimate strain of the samples, however, was approximately three to four times reported strain values for human valve samples. This indicated that the material can elongate more than a human sample before failure. While not all of the mechanical properties were the same, the similarities indicated that cellulose-based materials can be used as a heart valve substitute.

In addition, a composite material of cellulose with varying ratios of silicone (including, but not limited to, platinum-catalyzed) was tested using the same uni-axial extension tests. Adding silicone was hypothesized to increase the material's resistance to tearing. The results indicated that a ratio of approximately 60% cellulose to 40% silicone by weight had 60% greater stress at maximum load than samples of pure cellulose. The modulus of elasticity was also 170% greater than the pure cellulose sample. These values are within the standard deviation of mechanical properties reported for human aortic leaflet samples. A cellulose-silicone mixture can be desirable to resist higher loads encountered during in vivo conditions.

Mechanical properties of the cellulose-based material can be improved by optimizing the fabrication process (e.g., using different materials, different processes, etc.). Further, stent configurations can be optimized to allow for enhanced deliverability of the assemblies (e.g., using different materials, different shapes, etc.). In addition, various methods for attaching cellulose-based material to the frame can enhance performance. Durability testing can also be performed to test long term resistance to mechanical fatigue.

TABLE 1

Comparison of Human Aortic Valve to Cellulose-Based Prosthetic Assemblies

|  | Human Aortic Valve* | Pure Cellulose Membranes Created From Regeneration of Methylol Cellulose Solution** | Platinum Catalyzed Silicone and 62% Cellulose Membrane** |
|---|---|---|---|
| Thickness | 0.57 ± 0.16 mm | 0.49 mm | 0.21 mm |
| Width | 3.0 mm | 3.0 mm | 7.93 mm |
| Length | 20 mm | 20 mm | 24.62 mm |
| Modulus of Elasticity | Circumferential: @ 1 MPa, 15.34 ± 5.3 MPa Radial: @ 0.1 MPa, 1.98 ± 0.24 MPa | @ 1 MPa: 0.7305 MPa | @ 1 MPa: 1.9615 MPa |
| Ultimate Stress | Circumferential: 1.74 ± 0.37 MPa Radial: 0.32 ± 0.04 MPa | 0.9742 ± 0.298 MPa | 1.8524 ± 0.098 MPa |
| Ultimate Strain | Circumferential: 18.35 ± 7.61% Radial: 23.92 ± 4.87% | 98.81 ± 23.99% | 70.459 ± 10.46% |

*Stradins, P., Lacis, R., Ozolanta, I., Purina, B., Ose, V., Feldmane, L., et al. (2004). Comparison of biomechanical and structural properties between human aortic and pulmonary valve. *European Journal of Cardio-Thoracic Surgery*, 26, 634-639.
**Assuming isotropy (only tested in one orientation).

Figure 7:
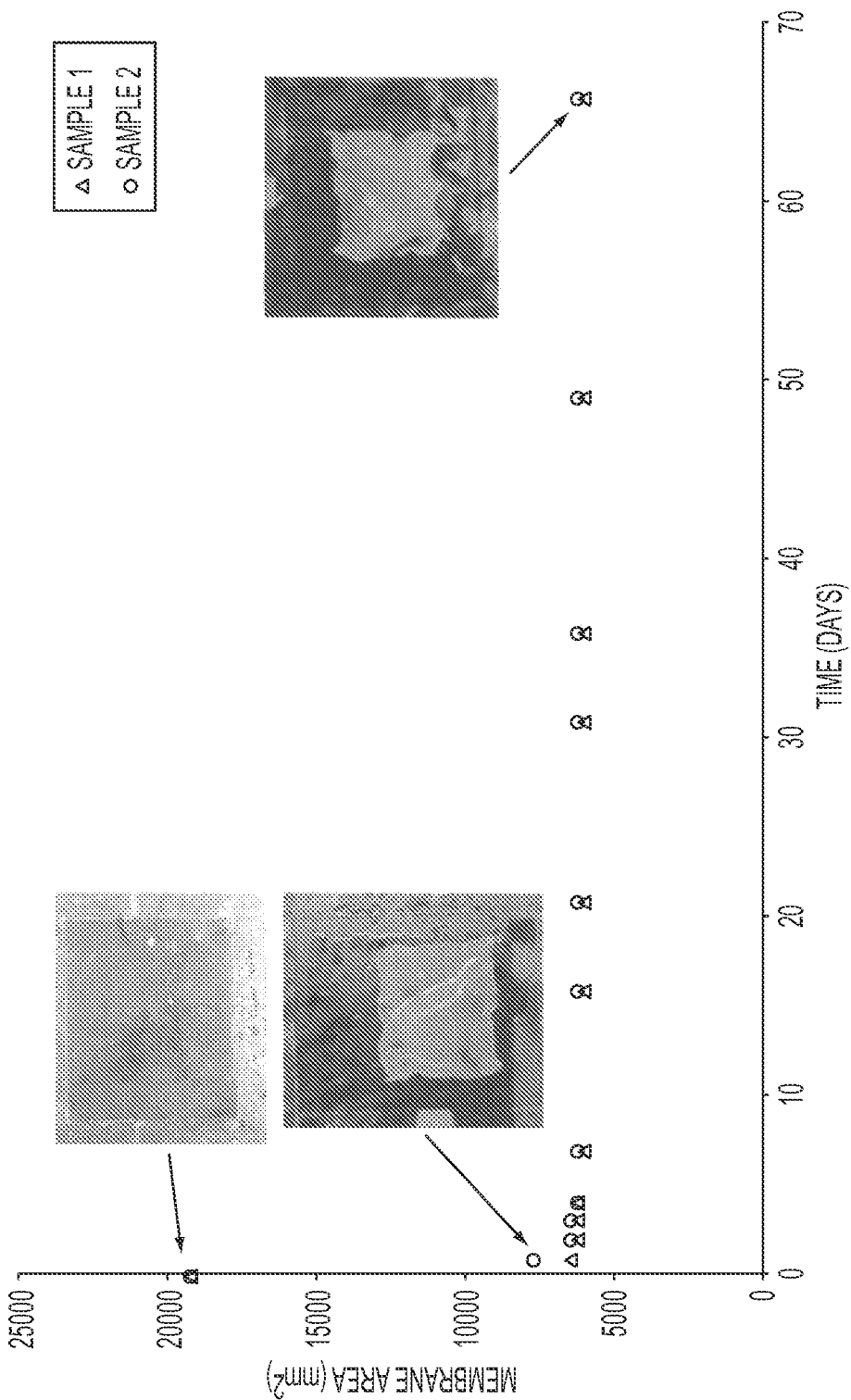
FIG. 7 depicts membrane area versus time for a long-term membrane regeneration stability study.

Long-term membrane regeneration stability studies were also performed on several samples. As depicted in FIG. 7, for example, it was determined that a methylolcellulose matrix membrane maintained its geometric configuration over extended periods of time when submerged in water.

Figure 8:
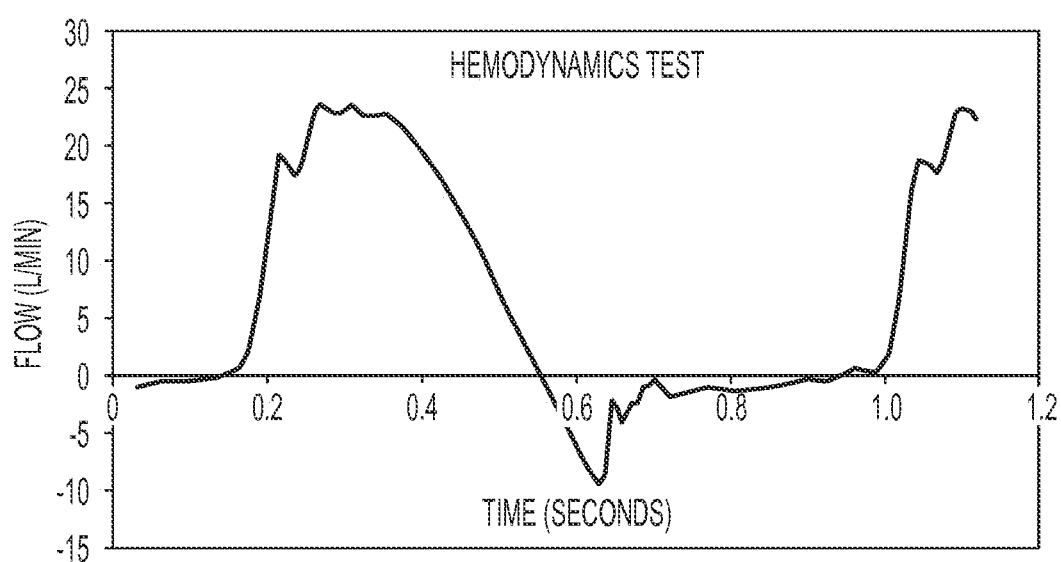
FIG. 8 depicts a pressure and flow diagram of one of the embodiments of the present assemblies.

Fluid dynamic testing was also performed on several embodiments of the present assemblies. A Vivitro Pulse Duplicator system was used to measure flow through the assemblies, the pressure gradient across the assemblies, the effective orifice area (EOA), and the assemblies' regurgitation value. For example, an assembly was deployed into a silicone tube representative of the geometry of a native heart valve. The radial force of the assembly's frame fixed the assembly within the apparatus. No migration was seen during the flow tests. Depicted in FIG. 8 is a pressure and flow diagram from a test using a saline solution. For the prototype valve dimensions, ISO 5840:2005 indicates a maximum regurgitation fraction of 15%. The regurgitation value for the assembly was measured to be 17.8%. Curve A of FIG. 8 resembles a curve seen by human aortic valves displaying a sharp increase in flow during contraction of the left ventricle. Once the valve closes, the profile gradually drops. A slight closing regurgitation is seen as the valve leaflets coapt. Curve B of FIG. 8 demonstrates the assembly's ability to maintain a pulse pressure of 40 mmHg (120 mmHg/80 mmHg). The assembly leaflets mimicked the motion of a healthy native valve. No significant wear was seen during testing.

Tests for deploying the assemblies were also performed. A nitinol frame with a pure (e.g., about 100%) cellulose body having a diameter of 25 mm was tested. An assembly was compressed using a crimping device and placed into a 21 Fr (about 7 mm) catheter. The catheter end containing the collapsed assembly was submerged into water that was heated to approximately body temperature. A catheter plunger tube was used to displace the assembly out of the inner lumen of the catheter and into the water. The assembly expanded to its pre-compressed diameter immediately. No damage to the frame or membrane occurred. The test was performed four times with similar results.

The above specification and examples provide a complete description of the structure, use and construction of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present assemblies are not intended to be limited to the particular forms disclosed. Rather, they include all modifications and alternatives falling within the scope of the claims, and embodiments other than the one shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The invention claimed is:

1. A method of manufacturing a vascular prosthetic assembly, the method comprising:
   pouring a cellulose-based mixture over a mandrel to form a first cellulose-based layer;
   submerging the first cellulose-based layer in a first liquid;
   placing a generally tubular frame around the first cellulose-based layer;
   pouring the cellulose-based mixture over the generally tubular frame and the first cellulose-based layer to form a second cellulose-based layer;
   submerging the first cellulose-based layer and the generally tubular frame, and the second cellulose-based layer in the first liquid; and
   submerging the first cellulose-based layer, the generally tubular frame, and the second cellulose-based layer in a second liquid.

2. The method of claim 1 wherein the first liquid is acetone.

3. The method of claim 1 wherein the second liquid is water.

* * * * *